United States Patent [19]
Milcamps

[11] Patent Number: 4,534,052
[45] Date of Patent: Aug. 6, 1985

[54] BLOCK FOR PARTIALLY LIMITING A RADIATION BEAM, AND A COLLIMATOR COMPRISING SUCH BLOCKS

[75] Inventor: Jacques Milcamps, Buc, France

[73] Assignee: C.G.R. - Mev, Buc, France

[21] Appl. No.: 481,784

[22] Filed: Apr. 4, 1983

[30] Foreign Application Priority Data

Apr. 2, 1982 [FR] France ................ 82 05785

[51] Int. Cl.³ .............................................. G21K 1/04
[52] U.S. Cl. ...................................... 378/152; 378/150
[58] Field of Search ............... 250/150, 152, 147, 159, 250/151, 505.1

[56] References Cited

U.S. PATENT DOCUMENTS

| | | | |
|---|---|---|---|
| 3,151,245 | 9/1964 | Wilson, Jr. | 378/152 |
| 3,980,407 | 9/1976 | Hill | 378/152 |
| 4,157,475 | 6/1979 | Stock et al. | 378/147 |

FOREIGN PATENT DOCUMENTS

| | | | |
|---|---|---|---|
| 1198194 | 8/1965 | Fed. Rep. of Germany . | |
| 1067753 | 5/1967 | United Kingdom | 350/150 |

*Primary Examiner*—Alfred E. Smith
*Assistant Examiner*—Carolyn E. Fields

[57] ABSTRACT

The invention provides a block for partially limiting a radiation beam, allowing a first part of this beam to be limited corresponding to a first maximum half angle of opening.

This rectilinearly movable block comprises a cylindrical active surface.

Because of this active surface, said block defines new limits for the beam without modifying the starting orientation of this active surface in dependence on the positions which it may occupy through its rectilinear movement.

9 Claims, 3 Drawing Figures

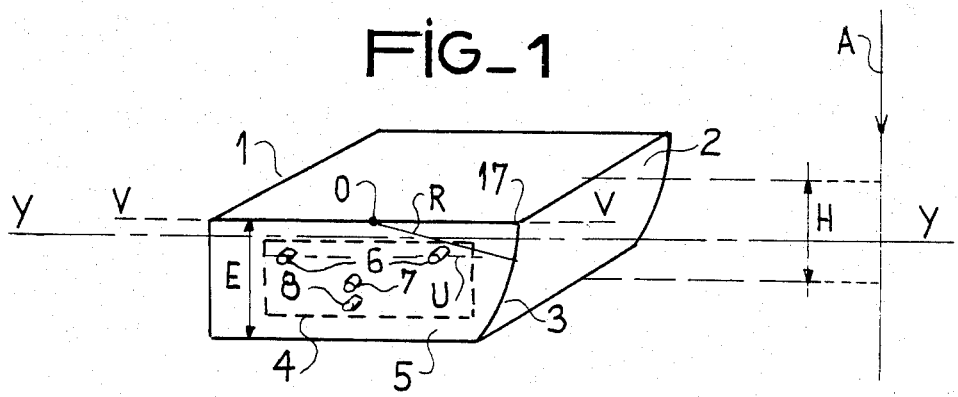
FIG_1
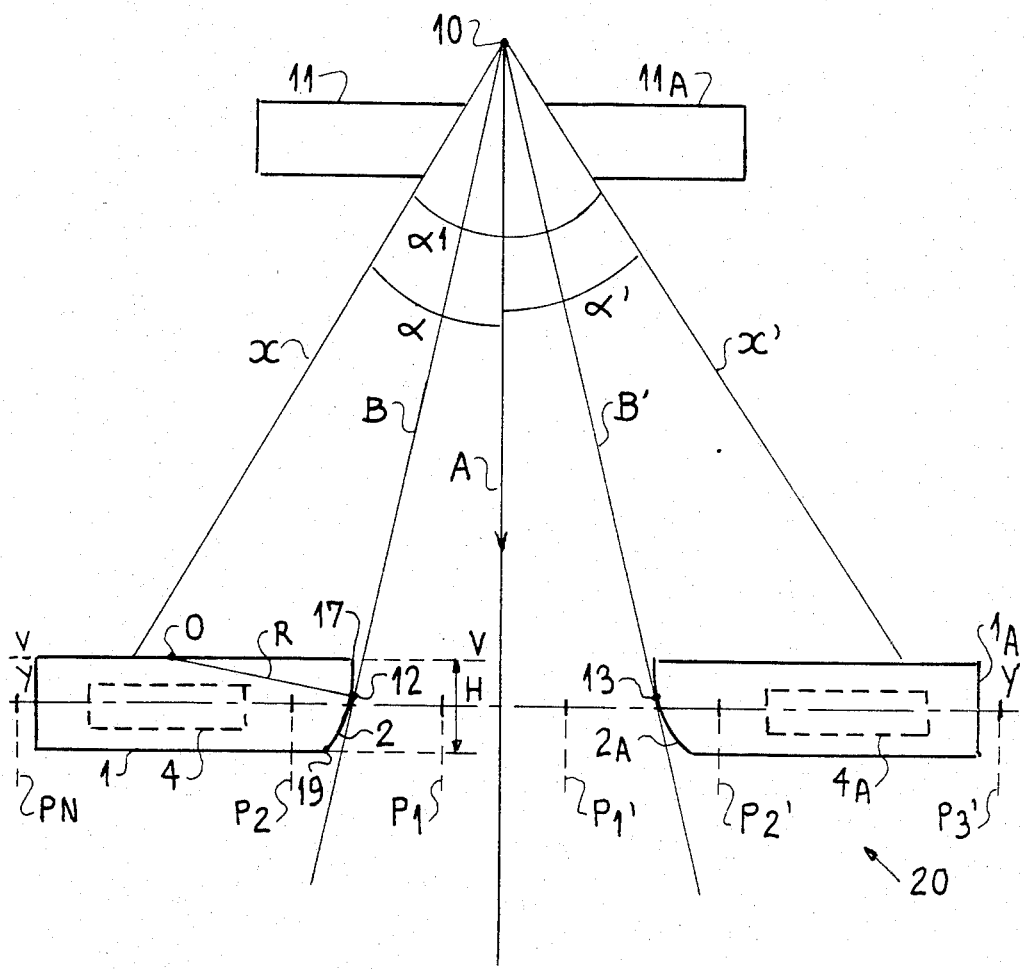
FIG_2

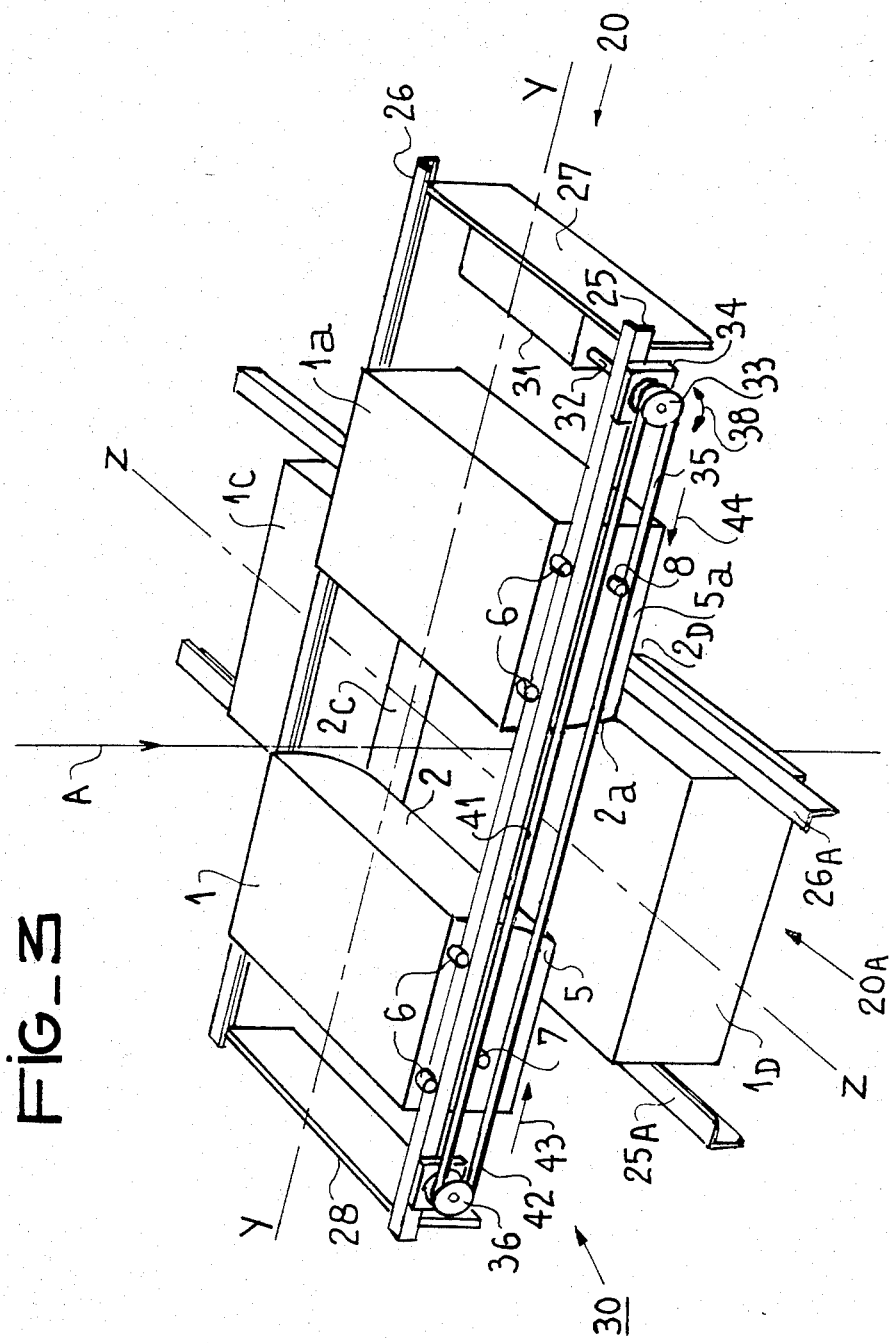

4,534,052

BLOCK FOR PARTIALLY LIMITING A RADIATION BEAM, AND A COLLIMATOR COMPRISING SUCH BLOCKS

BACKGROUND OF THE INVENTION

1. Field of the Invention

The invention relates to a block for partially limiting a radiation beam, providing this limitation with a reduced penumbra; it also relates to a space-saving collimator equipped with such blocks. Collimators are widely used in the radiotherapy field for example, where they allow the geometry of a useful beam to be defined with respect to a desired treatment area.

2. Description of the Prior Art

These collimators are generally formed by a first and second assembly for limiting the radiation beam, superimposed in the path of this latter and acting on two axes orthogonal and transversal to a reference direction of this beam, so as to delimit the useful beam. This first and second limiting assembly each comprise a first and a second movable partial limiting block, one end of which is intended to cut off a part of the beam; the spacing apart between these ends forming a slit into which passes the radiation beam. This beam is thus partially limited by passing through a first slit formed by the first limiting assembly and totally limited by passing through a second slit, formed by the second limiting assembly, at the output of which it forms the useful beam.

The position occupied by these first and second limiting devices, with respect to a reference direction of the radiation beam, defines a useful beam centered or off-centered with respect to this reference direction.

An important quality of the useful beam resides in its delimitation with a minimum penumbra; to this end, the ends intended to cut off the beam have a not inconsiderable thickness, which forms a flat surface called active surface in the description which follows. The orientation of this active surface, with respect to a source emitting the beam, is of great importance for obtaining the useful beam with a minimum penumbra.

This means that the orientation of the active surfaces may be modified for maintaining this orientation for each modification of the useful beam.

In the prior art, this condition is fulfilled by means of mechanical means and drive means whose construction is difficult and complicated. Thus, for example, a desired useful beam is obtained by a movement of the first and second limiting blocks such that their movement towards or away from each other is accompanied by a rocking movement of their longitudinal axis, so as to obtain correct orientation of the active surface which they comprise.

Taking into account a not inconsiderable length of these first and second limiting devices, the space required for allowing this rocking is large. A collimator thus formed has a volume which adversely affects the use thereof; furthermore, its assembly which is time-consuming and difficult requires costly machining operations, because of the complication of the mechanical and drive means used.

The present invention relates to a block for partially limiting a radiation beam, simple to mount and limiting a beam with a minimum penumbra because of its design which does not require the orientation of the active surface for each new position occupied by this block. It also relates to a collimator comprising such blocks in accordance with the invention, for determining the useful beam; a collimator in accordance with the invention takes up less space and is more simply assembled with respect to collimators of the prior art, its mechanical and drive means being simplified with respect to these latter.

SUMMARY OF THE INVENTION

The invention provides then a block for partially limiting a radiation beam emitted by a radiation source in a given reference direction, for limiting a first part of the beam corresponding to a maximum half angle of opening, wherein said limiting block is capable of a rectilinear movement parallel to a first axis transversal to the reference direction, comprising moving means and a cylindrical active surface, by which it defines for the beam a new limit depending on a position which it occupies along this first axis, so as to limit said beam with a minimum of penumbra, without modifying the orientation of the active surface as a function of the position which it occupies.

BRIEF DESCRIPTION OF THE DRAWINGS

The invention will be better understood from the following description, illustrated by the three accompanying figures in which:

FIG. 1 shows a perspective view of a limiting block in accordance with the invention;

FIG. 2 shows schematically a radiation source, associated with a limiting assembly formed by two limiting blocks in accordance with the invention; and FIG. 3 shows a perspective view of a collimator in accordance with the invention.

For the sake of clarity, the same elements bear the same references in all figures.

DESCRIPTION OF THE PREFERRED EMBODIMENT

FIG. 1 shows a first limiting block 1 in accordance with the invention, having a longitudinal axis Y—Y perpendicular to a reference direction A, in which is emitted a radiation beam (not shown in FIG. 1).

This limiting block 1 comprises an active surface 2 cylindrical in shape having as directrix an arc of a circle 3, formed by an edge of the active surface 2. The arc of a circle 3 comprises a center O situated on an axis V—V parallel to the longitudinal axis Y—Y and passing through one end 17 of the arc of a circle 3; since its radius R is determined by means of elements not shown in FIG. 1, it will be described further on in the description with reference to FIG. 2. In the non limiting example described, the active surface 2 comprises a height H equal to the thickness E of block 1, formed by the projection of the arc of a circle 3 and so of the active surface 2 on the reference direction A.

Block 1 also comprises moving means 4, shown in a broken line frame on one of its sides 5. The following description of these means 4 concerns the visible part of the figure, since the piece is symmetrical and a non visible side of block 1, opposite side 5, comprises the same means.

These moving means 4 comprise:

on the one hand guide means such as rolling rollers 6, situated on an axis U parallel to axis Y—Y, for cooperating with a path of movement (not shown in FIG. 1); this cooperation allowing the first limiting block 1 to move along the first axis Y—Y.

the moving means 4 further comprise securing means such as a stud 7 or 8 for securing block 1 to drive means (not shown), in a way which will be explained further on in the description.

FIG. 2 shows schematically the first limiting block 1 of the invention, associated with a second block 1A identical to the first one, these two blocks 1,1A forming a first limiting assembly 20 associated with a radiation source 10.

Source 10 generates a radiation beam in the reference direction A; this beam is delimited by a pre-collimator 11, 11A which defines for this beam a first limit X and a second limit X'.

These first and second limits X,X' present, with respect to the reference direction A, an angle α, α' forming a first and a second maximum half angle of opening of the beam, the sum of these angles α, α' forming the full opening angle α1.

The beam finds in its path the first and second blocks 1,1A, situated at positions P2,P2', on each side of the reference direction A, along the same first axis Y—Y. These blocks 1,1A may be moved manually or by motor means parallel to axis Y—Y, which in the non limiting example described allows them:

for block 1 to occupy N positions between positions P1,PN, and for block 1A, to occupy N' positions P1' to PN'. This symmetry of the positions of blocks 1,1A is shown by way of non limiting example, their positions being possibly assymetrical depending on the way in which their respective moving means 4,4A are associated with drive means (not shown).

In the non limiting example described, this travel of the limiting blocks 1,1A allows them to limit a first and a second part of the beam; the first part, limited by block 1, being located between the first limit X and the straight reference line A, corresponds to the first maximum half angle of opening α. The second part of the beam, limited by the second block 9, being located between the second limit X' and the straight reference line A, corresponds to the second maximum half angle of opening α'.

The first block 1 is thus capable of limiting this first part of the beam, by defining therefor new limits A,B, . . . X, depending on its position P1,P2, . . . PN, between the reference direction A and the first limit X; the second block 9 is able to limit the second part of the beam, by defining therefor new second limits A, B', . . . X', depending on its position P1',P2', . . . PN, between the reference direction A and the second limit X'.

These new limits are determined by the active surfaces 2,2A which, in the position occupied by the first and second blocks 1,1A in FIG. 2, define for the beam a first and a second new limit B,B'. These limits B,B', since they have source 1 as origin, are tangential to the cylindrical active surfaces 2,2A, at contact points 12, 13 situated on these active surfaces 2,2A. This tangential condition, which allows the beam to be limited with a maximum accuracy and a minimum penumbra, is maintained for all the limits A, B, . . . X and A,B', . . . X', because of a starting orientation of the active surfaces 2,2A.

It should be noted that, when blocks 1,6 occupy respectively the positions P1,P1', the beam is completely closed.

By taking as example the first limiting block 1, this example being also valid for the second limiting block 1A which has the same combination of means;

the orientation of the active surface 2 is determined by the position of the center O of the arc of a circle 3; this arc of a circle 3, shown in FIG. 1, merging in FIG. 2 with the active face 2. As has already been explained this center O is situated on an axis V—V passing through one end 17 of the arc of a circle 3; this end 17 being that one of the ends 17,19 the closest to source 10. Radius R is determined, on the one hand with respect to the maximum half angle of opening α of the beam and, on the other hand, by the height H of the active surface 2; this height H being generally imposed by conditions relative to the nature of the radiation beam and the absorption thereof.

Thus, this radius R in a limiting block 1 in accordance with the invention is determined by the following relationship:

$$R = H/\sin\alpha;$$

in which R is the radius of the arc of a circle 3, H is the height of the active surface 2, α is the value of the maximum half angle of opening.

This definition of the position of center O defines an orientation of the active surface 2 such that:

(a) with the first block 1 in the endmost position P1, the limit formed by the reference direction A is tangential to the active surface 2 at the endmost point 17, (b) with the first block 1 in the endmost position PN, the limit formed by the first limit X is tangential to the active surface 2 at the other endmost point 19; all the new limits A,B, . . . X being tangential to this active surface 2 at points located between these endmost points 17,19, as is shown in FIG. 2, where the new limit B is tangential to the active surface at point 12.

Such an arrangement is particularly advantageous in that it allows a part of a beam to be limited within desired limits A,B, . . . X by the rectilinear movement of the limiting block 1 of the invention without modifying the starting orientation of the active surface 2 as a function of the position P1,P2, . . . PN which block 1 may occupy. This arrangement is remarkable in that it allows the beam to be limited while retaining a minimum penumbra, whatever the positions P1, PN and P1',PN' occupied by blocks 1,6 may be; this penumbra never being greater than that obtained by devices of the prior art, which require a highly accurate orientation of their active surface, depending on the position which they occupy.

Thus, in the non limiting example described, each of the limiting blocks 1,1A limits a part of the beam such as represented by the first maximum half angle of opening α, for the first limiting block 1, and by the second maximum half angle of opening α' for the second block 1A. It is also possible for one of these blocks 1,1A to comprise a different starting orientation of its active surface 2,2A, depending on a different value of the first or of the second maximum half angle of opening α, α'; this allowing a useful beam, off-centered (not shown) with respect to the reference direction A, to be defined on the first axis Y—Y.

FIG. 3 shows a collimator 30 in accordance with the invention comprising on the first longitudinal axis Y—Y the first and the second limiting blocks 1,1A forming a first limiting assembly 20, such as already shown in FIG. 2; this collimator 30 comprising on a second axis Z—Z perpendicular to the first one a third and a fourth limiting block 1C, 1D, in accordance with the invention, these third and fourth blocks 1C,1D forming a second limiting assembly 20A identical to the first one.

These first and second limiting assemblies 20,20A are centered on the straight line A, defined above, and representing the reference direction of the beam.

The first limiting assembly 20 is associated with a rectilinear path of movement formed in the non limiting example of the description by rails 25,26 secured together at each end by a first and a second plate 27,28. The rolling means for the first and second blocks 1,1A formed by rollers 6 roll on these rails 25,26 disposed parallel to the first axis Y—Y.

These blocks 1,1A are driven by drive means which are simplified because of the rectilinear movement of these blocks 1,1A; in the non limiting example described, these drive means comprise a motor 31 whose rotation, in one direction or in the other, is transmitted through a shaft 32 to a first pulley 33; this latter is fixed to rail 25 by a bracket 34 and a conventional rolling means, not shown.

Rotation of the first pulley 33 is in the direction shown by arrow 38, in a plane parallel to that of sides 5,5A of the first and second blocks 1,1A. This rotation causes the movement of a chain or, as in the example described, a notched belt 35 passing round a return pulley 36; this defines for belt 35 an upper part 41 and a lower part 42 which are parallel and which have opposite directions of movement. This property is used for causing the movement of the first and second blocks 1,1A in a direction opposite to each other. For this purpose, the first block 1 is firmly secured to the upper part 41 of belt 35 by a stud 7 which is situated in the vicinity thereof; the second block 9 being firmly secured to the lower part 42 by stud 8. Setting motor 31 in rotation causes a movement of block 1 in the direction of arrow 43 when block 1A is moved in the direction of arrow 44, and vice versa. This allows a symmetrical travelling movement of the two blocks 1,1A, the symmetry being adjustable by positioning the attachment between studs 7,8 and belt 35.

Motor 31 may also control on rail 26 side a similar combination of drive means (not shown) as the one which has just been described.

A different arrangement, comprising for example for each limiting block 1,1A, a motor (not shown) allowing these blocks to be driven independently by motor in a simplified way because of the rectilinear movements of these blocks 1,1A is also possible.

The previously described motorization of the limiting assembly 20 is also valid for the limiting assembly 20A, whose third and fourth blocks 1C,1D are movable parallel to the axis Z—Z on rails 25A,26A; these blocks 1C,1D using a a similar combination of drive means (not shown) as that of limiting assembly 20.

With a collimator 30 in accordance with the invention, while being particularly space-saving, a useful beam may be delimited with a minimum penumbra and a maximum of accuracy. This saving of space is due to the simplification of the mechanical and drive means, since the movements of blocks 1, 1A and 1C,1D are rectilinear; this being made possible by the fact that these blocks comprise an active surface 2,2A,2C, 2D which does not require new orientations for each new position that these blocks occupy.

I claim:

1. A block for partially limiting a radiation beam emitted by a radiation source in a given reference direction, for limiting a first part of the beam corresponding to a maximum half angle of opening, said block being formed by a limiting block having moving means for allowing said limiting block to move in a parallel direction to a first axis transverse to said reference direction, said limiting block comprising a cylindrical active surface which defines limits for the beam, said limits being a function of the position which said cylindrical active surface occupies along said first axis, said moving means allowing movement of said limiting block such that the orientation of the active surface is not modified and said limits are tangential to the cylindrical active surface for all positions of said limiting block.

2. The limiting block as claimed in claim 1, wherein said cylindrical active surface comprises an edge in the form of an arc of a circle forming a directrix, whose projection on a straight reference line corresponding to said reference direction represents a height of said active surface.

3. The limiting block according to claim 2, wherein said arc of a circle comprises a radius determined by the following relationship:

$$R = H/\sin \alpha$$

R being the radius of the arc of a circle,
H being the height of the cylindrical active surface,
α being the angle representing the maximum half angle of opening of the beam.

4. The limiting block as claimed in claim 2, wherein said arc of a circle comprises a center O situated on an axis perpendicular to said reference direction and passing through the end of said arc of a circle the closest to said source.

5. The limiting block according to claim 4, wherein said arc of a circle comprises a radius determined by the following relationship:

$$R = H/\sin \alpha$$

R being the radius of the arc of a circle,
H being the height of the cylindrical active surface,
α being the angle representing the maximum half angle of opening of the beam.

6. In a collimator for delimiting a useful beam from a radiation beam, comprising a first limiting assembly having a first longitudinal axis transversal to the reference direction of the radiation beam, a second limiting assembly having a second longitudinal axis perpendicular to the first one and also transveral to the reference direction, these two assemblies being superimposed and centered on said direction, the first and the second limiting assemblies each comprise a first and a second limiting block such as claimed in one of the preceding claims, cooperating with paths of rectilinear movement, for allowing said limiting blocks to move along the longitudinal axis of the assembly to which they belong.

7. The collimator as claimed in claim 6, wherein said paths of movement cooperate with rolling means formed by rollers which said limiting blocks comprise so as to allow rectilinear movement of these blocks.

8. The collimator as claimed in claim 7, further comprising drive means cooperating with studs for securing said limiting blocks so as to ensure the motorized movements of said limiting blocks.

9. The collimator as claimed in claim 6, further comprising drive means cooperating with studs for securing said limiting blocks so as to ensure the motorized movements of said limiting blocks.

* * * * *